US008328864B2

(12) United States Patent
Niermann

(10) Patent No.: US 8,328,864 B2
(45) Date of Patent: Dec. 11, 2012

(54) STENT HAVING PHASED HOOP SECTIONS

(75) Inventor: Volker Niermann, Bound Brook, NJ (US)

(73) Assignee: Cordis Corporation

( * ) Notice: Subject to any disclaimer, the term of this patent is extended or adjusted under 35 U.S.C. 154(b) by 319 days.

(21) Appl. No.: 11/259,565

(22) Filed: Oct. 26, 2005

(65) Prior Publication Data

US 2006/0095113 A1 May 4, 2006

Related U.S. Application Data

(60) Provisional application No. 60/622,196, filed on Oct. 26, 2004.

(51) Int. Cl.
*A61F 2/06* (2006.01)
(52) U.S. Cl. ...................... 623/1.16; 623/1.15
(58) Field of Classification Search ............... 623/23.7, 623/1.15–1.16, 1.17–1.22
See application file for complete search history.

(56) References Cited

U.S. PATENT DOCUMENTS

| 5,911,754 | A | * | 6/1999 | Kanesaka et al. | 623/1.15 |
| 6,042,597 | A | * | 3/2000 | Kveen et al. | 623/1.15 |
| 6,190,403 | B1 | * | 2/2001 | Fischell et al. | 623/1.16 |
| 6,471,720 | B1 | | 10/2002 | Ehr et al. | |
| 6,540,775 | B1 | * | 4/2003 | Fischell et al. | 623/1.15 |
| 7,431,732 | B2 | * | 10/2008 | Moriuchi et al. | 623/1.15 |
| 2003/0083731 | A1 | * | 5/2003 | Kramer et al. | 623/1.15 |
| 2004/0133271 | A1 | | 7/2004 | Jang | |
| 2006/0030928 | A1 | * | 2/2006 | Burgermeister et al. | 623/1.15 |

FOREIGN PATENT DOCUMENTS

| EP | 1374800 A | 1/2004 |
| WO | WO 00/30563 A1 | 6/2000 |
| WO | WO 2004/075790 A1 | 9/2004 |

OTHER PUBLICATIONS

International Search Report re: PCT/US2005/038768 dated Feb. 24, 2006.
Japanese Notification of Reasons for Refusal mailed on Mar. 1, 2011 from corresponding Japanese Patent Application No. 2007-539108.

* cited by examiner

*Primary Examiner* — Corrine M McDermott
*Assistant Examiner* — Gregory Anderson

(57) ABSTRACT

This invention relates generally to an expandable intraluminal medical device for use within a body passageway or duct, and more particularly to a stent having at least a first hoop section and a second hoop section. The first hoop section comprises a tubular configuration of structural elements having proximal and distal open end, and defining a longitudinal axis extending there between. The second hoop section comprises a tubular configuration of structural elements having proximal and distal open end, and extending along the longitudinal axis defined by the first hoop section, but is rotationally offset from the first hoop section about the longitudinal axis.

11 Claims, 10 Drawing Sheets

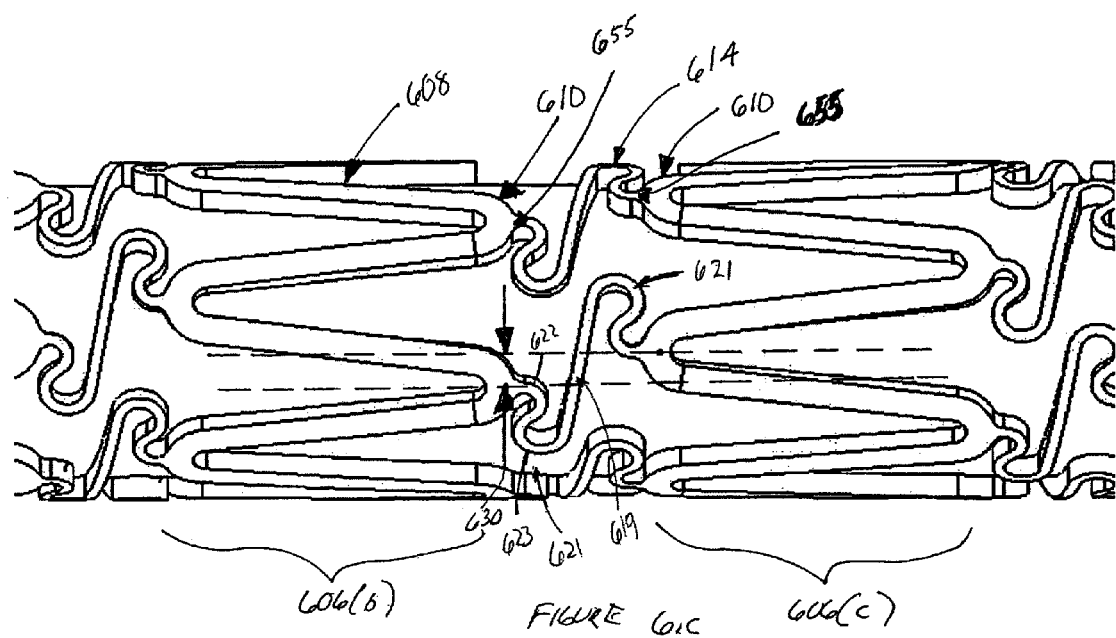

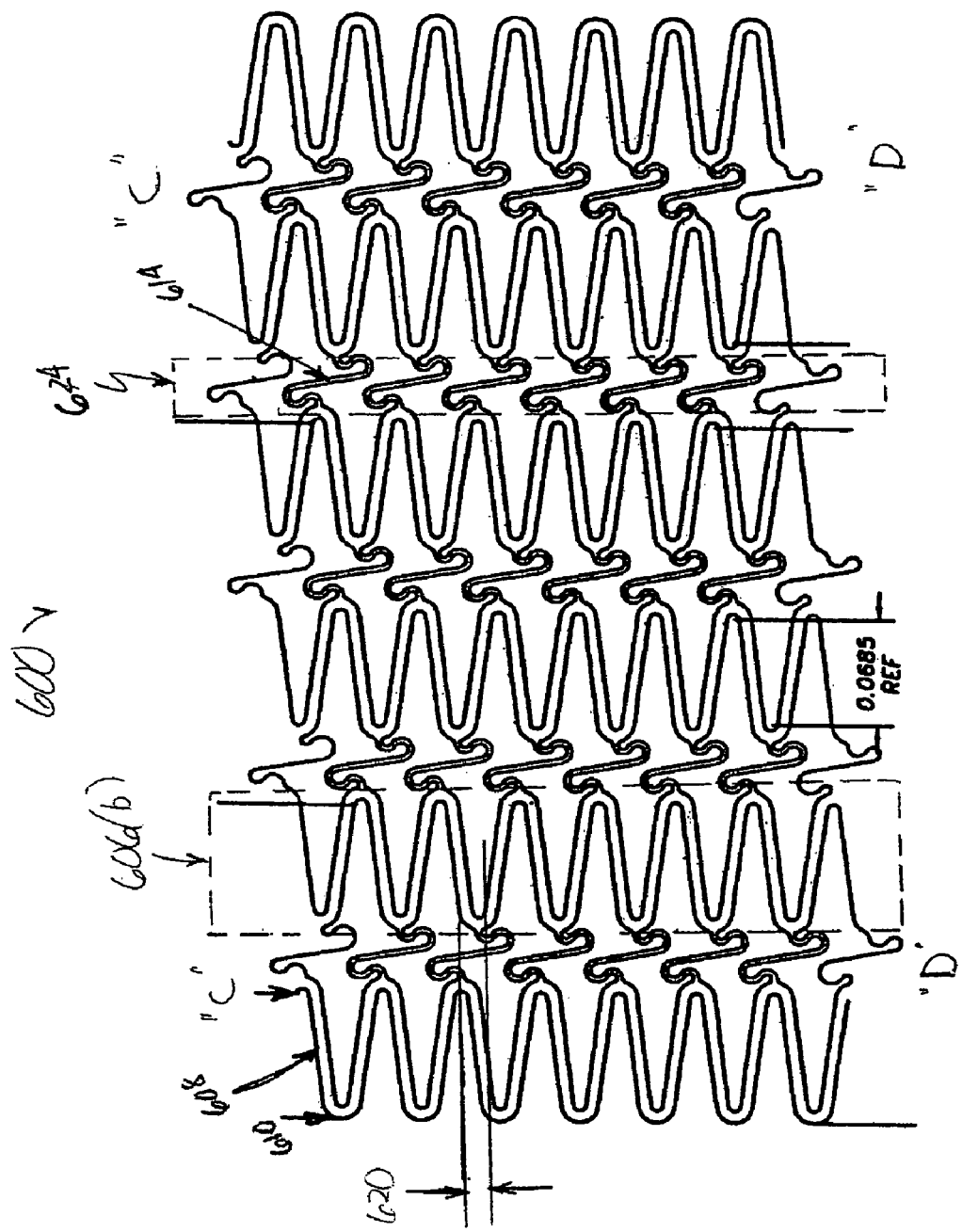

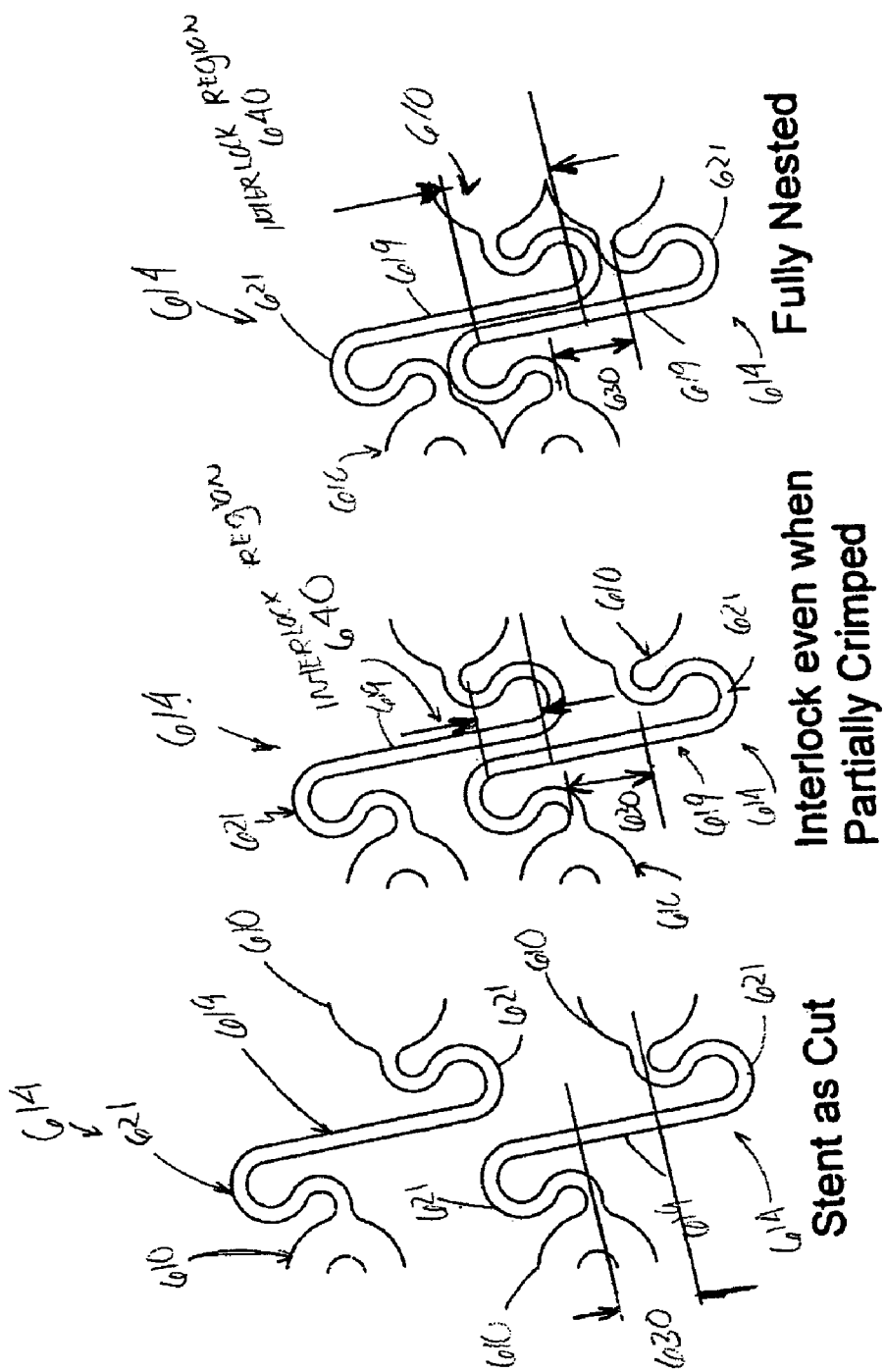

STENT HAVING PHASED HOOP SECTIONS

CROSS-REFERENCE TO RELATED APPLICATIONS

This application claims priority pursuant to 35 U.S.C. §119(e) to provisional application 60/622,196 filed on Oct. 26, 2004.

FIELD OF THE INVENTION

This invention relates generally to expandable intraluminal medical devices for use within a body passageway or duct, and more particularly to a stent having adjacent hoop sections that are rotationally out of phase, providing flexible links that minimize foreshortening during stent deployment.

BACKGROUND OF THE INVENTION

The use of intraluminal prosthetic devices has been demonstrated to present an alternative to conventional vascular surgery. Intraluminal prosthetic devices are commonly used in the repair of aneurysms, as liners for vessels, or to provide mechanical support to prevent the collapse of stenosed or occluded vessels.

Intraluminal endovascular prosthetics involves the percutaneous insertion of a generally tubular prosthetic device, such as a stent, into a vessel or other tubular structure within the vascular system. The stent is typically delivered to a specific location inside the vascular system in a compressed state by a catheter. Once delivered to the desired location, the stent is deployed by expanding the stent into the vessel wall. The expanded stent typically has a diameter that is several times larger than the diameter of the stent in its compressed state. The expansion of the stent may be performed by several methods known in the art, such as by a mechanical expansion device (balloon catheter expansion stent) or by self-expansion.

The positioning of the stent within the vessel is a critical factor that affects the performance of the stent and the success of the medical procedure. Since the region in the vessel lumen at which the stent is to be deployed is usually very difficult for a physician to access, it is essential that the stent's deployed diameter and length be known before the physician can accurately position the correctly sized device.

Careful sizing of the correct stent for the desired region of the vessel lumen may be a difficult challenge for many physicians. Although the dimensions of the body vessel at the region may be known, uncertainty about the stent's exact deployed diameter and length may lead to less than optimal performance. One cause for uncertainty in the stent's deployed diameter and length is a condition known as foreshortening.

Foreshortening can be better understood by defining the condition within the context of change in the stent length before and after deployment. For the purpose of this definition, "crimped length" describes the starting point of the stent—that is the length of the unexpanded stent mounted on a delivery catheter prior to deployment. The term "deployed length" is defined at the clinical end point of change—that is the length of the stent deployed within the lumen. Foreshortening is equivalent to the distance between these two points, i.e. the difference between the contained ("crimped") and deployed length.

Foreshortening occurs to varying degrees with all stents. This is especially true for endovascular stents greater than 4 millimeters in diameter. The amount of stent foreshortening is determined predominately by how the particular stent design accommodates expansion. For example, self-expanding stents are commonly deployed by operation of a retractable sheath. As the sheath is retracted the distal end of the stent is released first. Foreshortening can occur within this distal segment until the stent anchors on the lumen wall. As the sheath retraction continues, the proximal segment will foreshorten as it is deployed.

Balloon-expandable stents also foreshorten during expansion. Stents deployed by standard catheter balloons invariably see the balloon inflate at the weakest section first. Typically, the weakest section of the balloon will be at the exposed distal and/or proximal ends, i.e. the sections of the balloon not supported directly by the catheter or the stent. Accordingly, as the balloon is expanded the proximal end and/or distal end(s) of the balloon will inflate first. The inflated end(s) of the stent will experience the pressure of the balloon pressing outward in a radial direction to expand the stent, and also inwardly in an axial compressive direction. This axial compressive force causes the weaker connecting links or "flex links" of the stent to compress, causing the stent to foreshorten.

What is needed is an intraluminal medical device that will accommodate the device expansion into the wall of the lumen, while minimizing device foreshortening.

SUMMARY OF THE INVENTION

This invention relates generally to expandable intraluminal medical devices for use within a body passageway or duct, and more particularly to a stent having adjacent hoop structures that are rotationally out of phase, providing flexible links that minimize foreshortening during stent deployment.

In one embodiment of the present invention the intraluminal prosthetic device includes a first hoop section having a first circumferential phase orientation along a longitudinal axis and a second hoop section having a second circumferential phase orientation along the longitudinal axis. The first circumferential phase orientation is different than the second circumferential phase orientation. The prosthetic device additionally includes at least one flex member having a first and a second end. The first end of each flex member is attached to the first hoop section and the second end of each flex member is attached to the second hoop section.

In another embodiment of the present invention, the intraluminal prosthetic device includes a first hoop section comprising a plurality of first loop members and a second hoop comprising a plurality of second loop members. The hoop sections are oriented such that the first loop members are not axially aligned with the second loop members. The prosthetic device also includes at least one flex member having a first and a second end, wherein the first end of each flex member is attached to the first loop and the second end of each flex member is attached to the second loop.

In still a further embodiment of the present invention, the intraluminal prosthetic device includes a first and a second hoop section comprising a tubular configuration of structural elements having proximal and distal open end, and defining a longitudinal axis extending there between. The first and the second hoop sections are oriented such that the second hoop section is rotationally offset from the first hoop section about the longitudinal axis. The prosthetic device also includes at least one flex member having a first and a second end, wherein the first end of each flex member is attached to the distal end of the first hoop section and the second end of each flex member is attached to the proximal end of the second hoop section.

BRIEF DESCRIPTION OF THE DRAWINGS

FIG. 6C is a magnified perspective views illustrating the structural element comprising a stent according to one embodiment of the present invention.

FIG. 6D illustrates a stent according to one embodiment of the present invention, as it would appear if it were cut longitudinally and then laid out flat in a 2-dimensional configuration.

FIG. 6E illustrates the relationship between circumferentially adjacent flex links when a stent, according to one embodiment of the present invention, is in the cut, fully expanded configuration.

FIG. 6F illustrates the relationship between circumferentially adjacent flex links when a stent, according to one embodiment of the present invention, is in the partially crimped configuration.

FIG. 6G illustrates the relationship between circumferentially adjacent flex links when a stent, according to one embodiment of the present invention, is in the fully nested configuration.

DETAILED DESCRIPTION OF THE INVENTION

Figure 1:
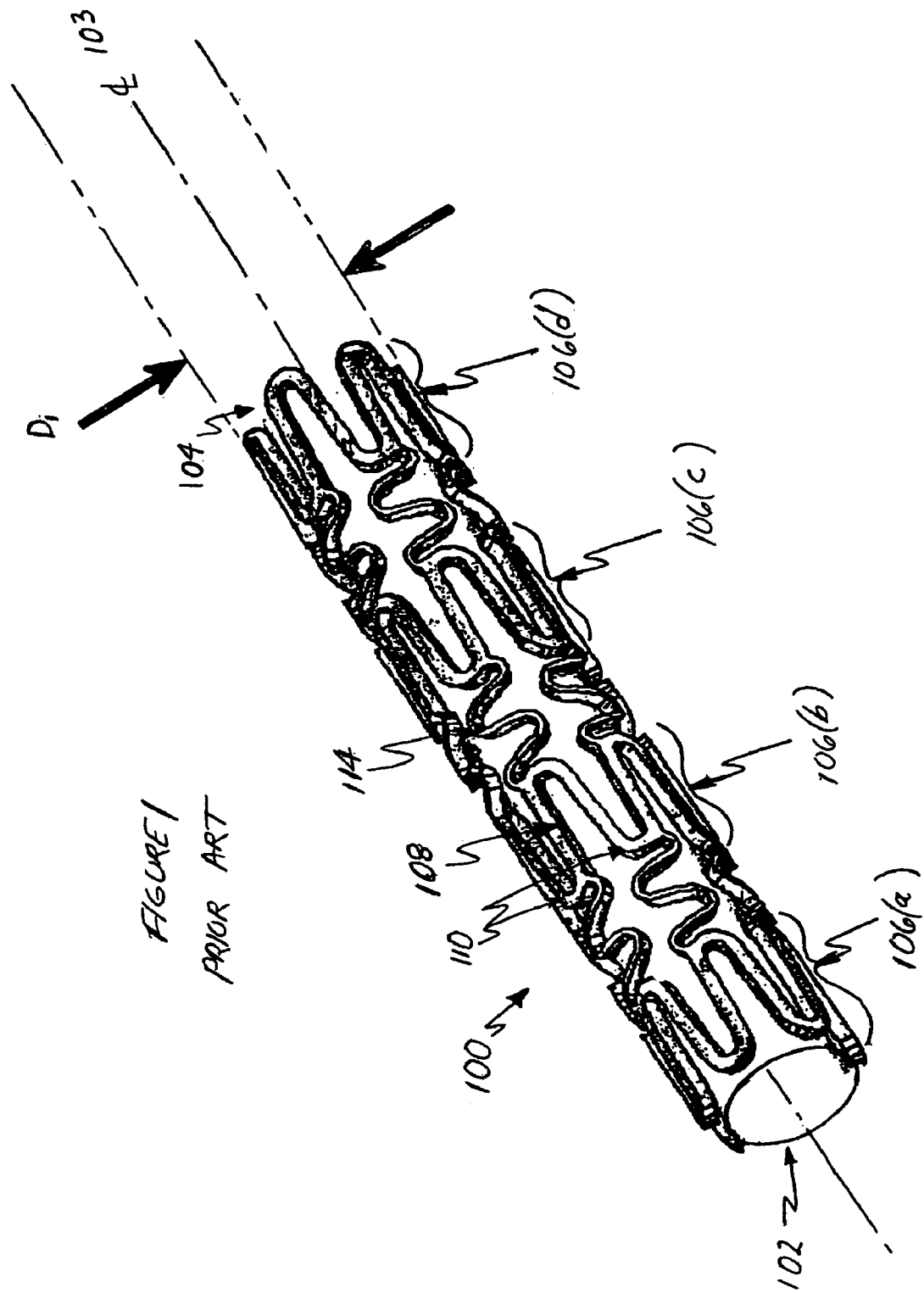
FIG. 1 illustrates a perspective view of an exemplary stent in an unexpanded or crimped, pre-deployed state.

The present invention describes an intraluminal medical device having phased structural sections that will accommodate the device expansion into the wall of a vessel lumen, while minimizing foreshortening of the device caused by axial compression of the device components. An intravascular stent will be described for the purpose of example. However, as the term is used herein, intraluminal medical device includes but is not limited to any expandable intravascular prosthesis, expandable intraluminal vascular graft, stent, or any other mechanical scaffolding device used to maintain or expand a body passageway. Further, in this regard, the term "body passageway" encompasses any duct within a mammalian's body, or any body vessel including but not limited to any vein, artery, duct, vessel, passageway, trachea, ureters, esophagus, as well as any artificial vessel such as grafts.

The structure and flexible-component according to the present invention may be incorporated into any radially expandable stent design, including self-expanding stents and mechanically expanded stents. Mechanically expanded stents include, but are not limited to stents that are radially expanded by an expansion member, such as by the expansion of a balloon.

With reference to the drawing figures, like parts are represented by like reference numerals throughout the various different figures. By way of example, strut 108 in FIG. 1 is equivalent to strut 308 in FIG. 3.

Figure 2:
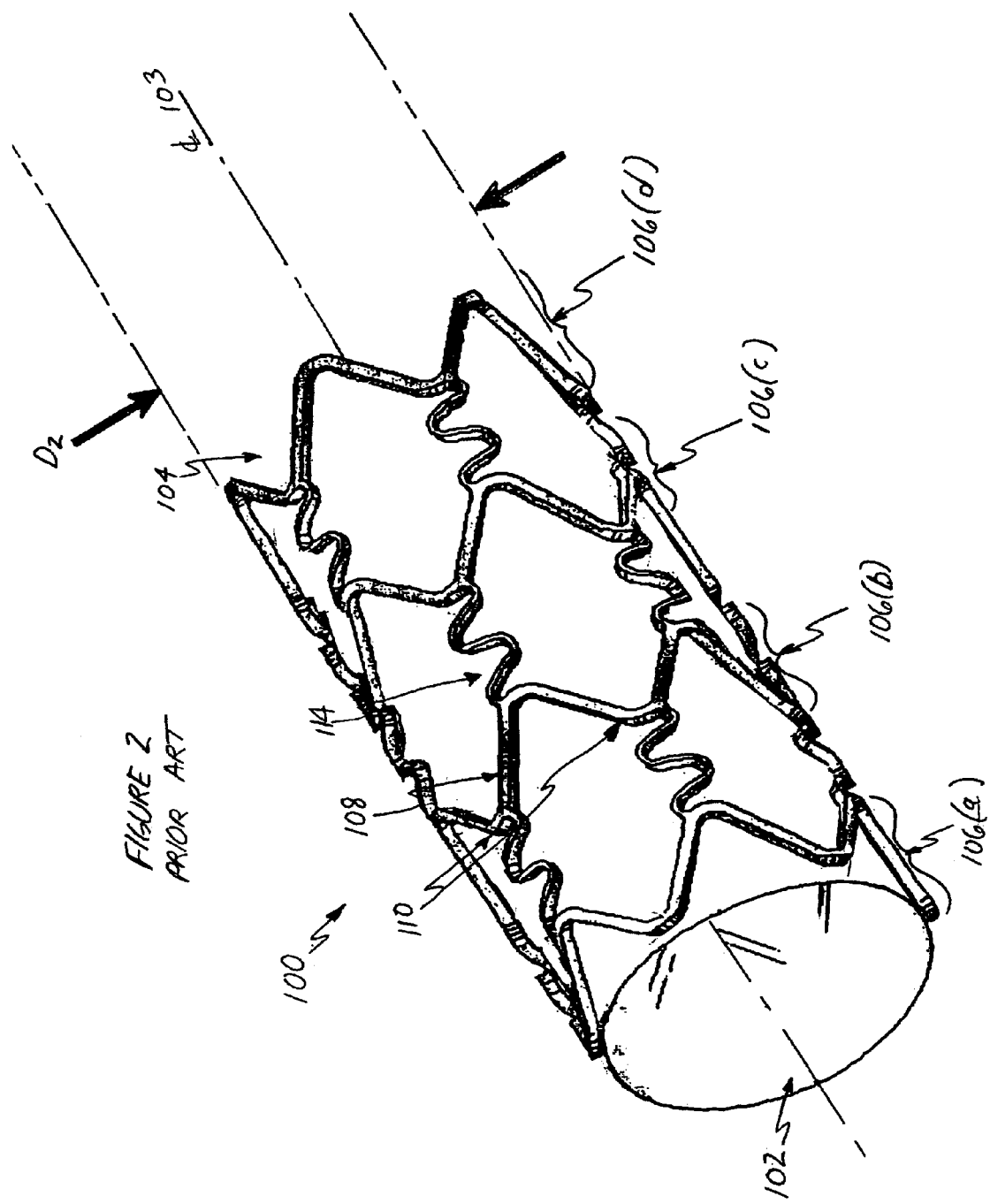
FIG. 2 illustrates a perspective view of an exemplary stent in an expanded, deployed state.
Figure 3:
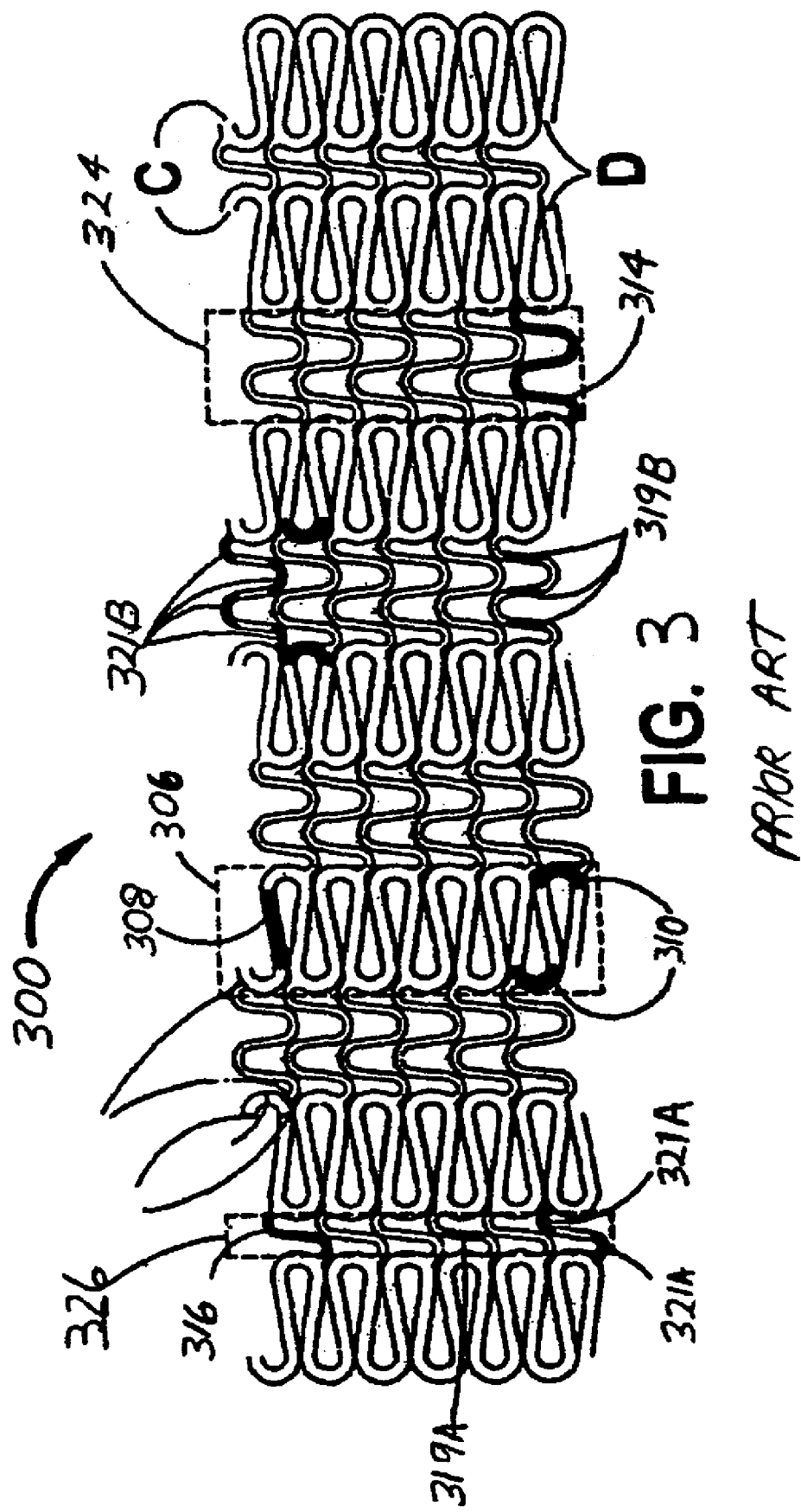
FIG. 3 illustrates a two-dimensional view of an exemplary stent in its crimped, pre-deployed configuration, as it would appear if it were cut longitudinally and then laid out flat.
Figure 4A:
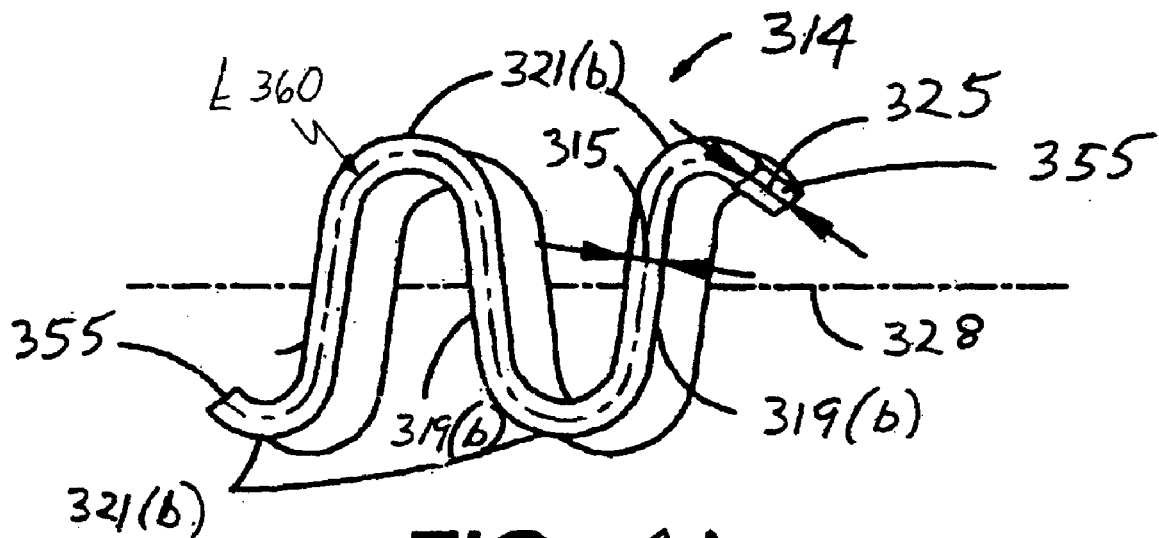
FIG. 4A illustrates a perspective view of an exemplary prior art "N" flex link.
Figure 4B:
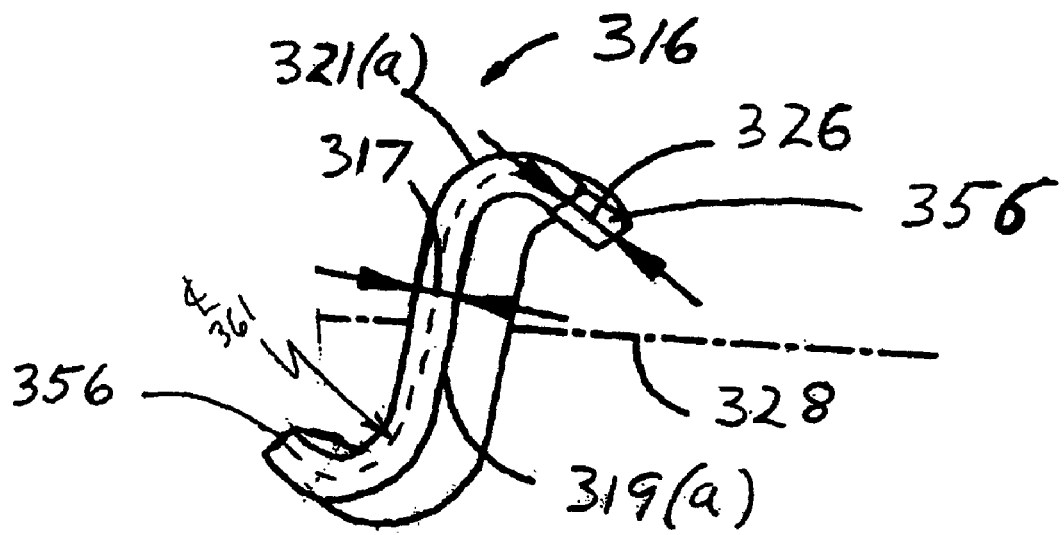
FIG. 4B illustrates a perspective view of an exemplary prior art "J" flex link.
Figure 5:
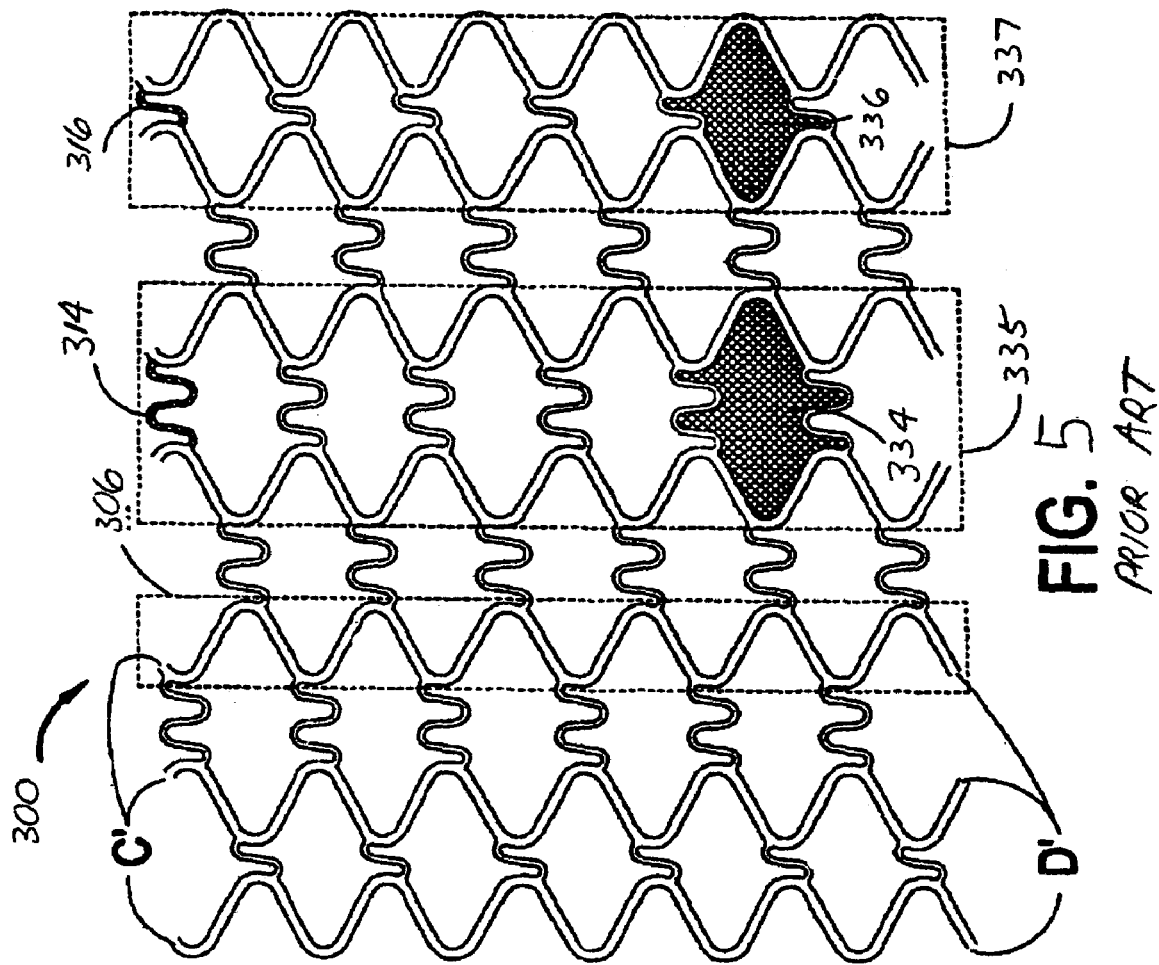
FIG. 5 illustrates a two-dimensional view of an exemplary stent in its expanded, deployed configuration as it would appear if it were cut longitudinally and then laid out flat.

Referring to FIGS. 1-5, there are illustrated exemplary stents 100, 300 as are known in the art. FIGS. 1 and 3 illustrate typical prior art stents 100, 300 in an unexpanded or crimped, pre-deployed state, while FIGS. 2 and 5 show the stents 100, 300 in the fully expanded state. Although Z or S shaped pattern stents are shown for the purpose of example, the illustration is not to be construed as limiting the scope of this invention.

Turning now to FIGS. 1 and 2, a stent 100 comprises a tubular configuration of structural elements having proximal and distal open ends 102, 104 and defining a longitudinal axis 103 extending there between. The stent 100 has a first diameter D1 for insertion into a patient and navigation through the vessels, and a second diameter D2 for deployment into the target area of a vessel, with the second diameter being greater than the first diameter.

The stent 100 structure comprises a plurality of adjacent hoops 106(a)-(d) extending between the proximal and distal ends 102, 104. The hoops 106(a)-(d) include a plurality of longitudinally arranged strut members 108 and a plurality of loop members 110 connecting adjacent struts 108. Adjacent struts 108 are connected at opposite ends in a substantially S or Z shaped pattern so as to form a plurality of cells. However, one of ordinary skill in the art would recognize that the pattern shaped by the struts is not a limiting factor in this invention, and other shaped patterns may be used. The plurality of loops 110 have a substantially semi-circular configuration and are substantially symmetric about their centers. Adjacent hoop sections 106 (a)-(d) are in the same circumferential orientation. That is to say, adjacent loop members 110 are axially aligned along the longitudinal axis.

The stent 100 structure further comprises a plurality of bridge members or flex links 114, which connect adjacent hoops 106(a)-(d). Each flex link 114 comprises two ends. Each one end of each flex link 114 is attached to one loop 110 on one hoop, for example hoop 106(c), and the other end of each flex link 114 is attached to one loop 110 on an adjacent hoop, for example hoop 106(d). The flex links 114 connect adjacent hoops 106(a)-(d) together at flex link to loop connection regions.

The Figures generally show a stent having a closed cell design, with the flex links 114 connected to the adjacent hoop 106 at each loop 110. In any of the described configurations, the connections between the hoop structures 106 and the adjacent flex link 114 may be made at every loop member 110; or alternatively, at a subset of the loop members 110 around the circumference of the hoop 106. In other words, the connected loop members 110 may alternate with unconnected loop members 110 in some defined pattern around the circumference of hoop section 106.

FIGS. 3 and 5 illustrate a typical stent 300 as is know in the prior art. As shown in FIG. 3, stent 300 is in its crimped, pre-deployed state, as it would appear if it were cut longitudinally and then laid out flat in a 2-dimensional configuration. Similarly, stent 300 in FIG. 5 is a 2-dimensional representation of the cylindrical stent 300 after deployment; i.e. after radially outward expansion. It should be clearly understood that the stent 300 depicted in FIGS. 3 and 5 is in fact cylindrical in shape, similar to stent 100 shown in FIG. 1, and is only shown in the flat configuration for the purpose of illustration. This cylindrical shape would be obtained by rolling the flat configuration of FIGS. 3 and 5 into a cylinder with the top points "C" joined to the bottom points "D".

The stent 300 is typically fabricated by laser machining of a cylindrical, stainless steel tube. However, one of skill in the art would understand that other materials may be used to fabricate the stent, including, for example, Nitinol or Cobalt-Chromium alloys.

A set of strut members (as shown within the dotted rectangle) form a closed, cylindrical, hoop section 306 of the stent 300, similar to hoop 106(c) of FIG. 1. As described earlier, the hoop section 306 comprises a plurality of loop members 310 connected by longitudinally arranged strut members 308. The hoop section 306 can be said to consist of a multiplicity of strut elements with each strut element consisting of one loop member 310 joined to one strut 308.

Except at the extreme ends of the stent 300, every curved loop member 310 in adjacent hoops 306 are attached to a flex link that is either an "N" flex link 314 or a "J" flex link 316. A stent 300 that is thus fully connected is called a "closed cell" stent. However other open and closed cell designs are also contemplated by the present invention such that every curved loop member 310 may not be attached to a flex link. For example, the connections between the hoop structures 306 and the adjacent flex link 314 may be made at every loop member 310; or alternatively, at a subset of the loop members 310 around the circumference of the hoop 306. In other words, the connected loop members 310 may alternate with unconnected loop members 310 in some defined pattern around the circumference of hoop section 306.

FIG. 5 shows deployed structural cells 336 having two of the "J" flex links 316 on their perimeter, and deployed special expandable cells 334 having two of the flexible "N" flex links 314 on their perimeter. As noted above, circumferentially extending sets of cells are formed into hoop-like, circumferential cylindrical sections (hoop sections 306) with (in this case) exactly six cells per cylindrical segment. Typically a multi-cell stent would have at least three cells per hoop section. The stent 300 illustrated in FIGS. 3 and 5 has exactly two cylindrical hoops (illustrated in the flat as sections 337) of structural cells 336, and four cylindrical sections 335 of expandable cells 334.

Another way to describe the fully connected configuration of the stent 300 is as multiple longitudinally spaced sets of hoop sections 306 inter-connected by either sets of flexible "N" flex links 324 or sets of flexible "J" flex links 326. Each set of "N" flex links 324 comprises multiple circumferentially spaced "N" flex links 314 with each "N" flex link 314 being connected to two curved loop members 310 of adjacent hoop sections 306. The number of "N" flex links 314 in the set of "N" flex links 324 is no more than one-half of the total number of curved loop members 310 in the loop section 306.

Similarly, each set of flexible "J" flex links 326 consists of multiple circumferentially spaced "J" flex links 316 with each "J" flex link being connected to two curved loop members 310 of the hoop section 306. The number of "J" flex links 316 in the set of "J" flex links 326 is no more than one half of the total number of curved loop members 310 in the hoop section 306. As earlier described, FIGS. 3 and 5 illustrate adjacent hoop sections 306, 506 in the same circumferential orientation. That is, adjacent loop members 310, 510 on adjacent hoop sections are in axial alignment.

FIGS. 4A and 4B show 3-dimensional, perspective views of the "N" flex link 314 and the "J" flex link 316 of the stent 300 respectively. The "N" link 314 comprises four generally longitudinally extending curved segments 321(b) connected by three generally circumferentially extending segments 319(b) with each "N" flex link 314 having two ends that are attached to curved loop members 310 at attachment points 355. The "N" flex link 314 shown in FIG. 4A has a strut width 315 as measured in a direction that is generally along the surface of the stent that is smaller than the wall thickness 325 as measured in a radial direction from the stent's longitudinal axis 328. Also illustrated in FIG. 4A is the centerline length 360 of the N flex link 314. The centerline length is directly proportional to flexibility of the flex link.

The strut width 315 for a stent is typically less than 0.10 mm to provide good flexibility while the wall thickness 325 is typically greater than 0.10 mm to provide good stent radiopacity. Ideally the ratio of the width 315 to the thickness 325 is less than 1.0 and preferably less than 0.8. For a stent, the nominal strut width 315 would typically be 0.08 mm and the nominal wall thickness 325 is typically 0.12 mm.

The combination of thin strut width 315 and thick wall thickness 325 allows the "N" flex link 314 to easily lengthen and shorten for increased stent flexibility while making the "IN" flex link 314 relatively stiff with respect to bulging inward into the lumen of the stent 300. This stiffness enhances the ability of the "N" flex link 314 to push outward against plaque in a coronary artery after the stent 300 is deployed. In addition it was thought that the thin width 315 of the "N" flex link 314 would allow the flex link 314 to stretch during stent expansion, reducing the foreshortening of the stent 300. However, this axial flexibility contributes to the stent foreshortening.

As illustrated in FIG. 4B, each "J" link 316 consists of two generally longitudinally extending curved segments 321(a) connected by a straight circumferential segment 319(a), with each "J" flex link 316 having two ends that are identically attached to curved loop members 310 at attachment points 356. The "J" flex link 316 shown in FIG. 4B has a strut width 317 as measured in a direction that is generally along the surface of the stent that is smaller than the wall thickness 326 as measured in a radial direction from the stent's longitudinal axis 328. Also illustrated in FIG. 4B is the centerline length 361 of the "J" flex link 316. The centerline length is directly proportional to the flexibility of the flex link.

As previously described, the stent 300 shown in FIGS. 3 and 5 can be said to have adjacent hoop sections 306 that are connected either by multiple "N" flex links 314 or by multiple "J" flex links 316. Each "N" flex link 314 is shaped so as to nest together into the adjacent "N" flex link 314 as is clearly illustrated in FIG. 3. "Nesting" is defined as having the top of a first flexible link inserted beyond the bottom of a second flexible link situated just above that first flexible link. Similarly, the bottom of the first flexible link is inserted just below the top of a third flexible link that is situated just below the first flexible link. Thus, a stent with nested individual flexible links has each individual flexible link nested into both adjacent flexible links; i.e., the flexible link directly below and the flexible link directly above that individual flexible link. This nesting permits crimping of the stent 300 to smaller diameters without having the "N" flex links 314 overlap.

Since stents similar to stent 300 are delivered percutaneously into a body lumen, the flex links are designed to allow stent 300 to bend with relative ease as it goes around curved arteries and vessels. To provide this necessary flexibility, the "N" flex links 314 lengthen on the outside of the bent stent 300 and shorten on the inside of the bent stent 300 as the stent 300 traverses through the lumen. This increased flexibility, while necessary to percutaneously deliver the stent 300 to its desired location, may also contribute to the foreshortening effect described earlier.

While a stent is deploying (opening), the stent's flex connectors start to stretch and compensate for the foreshortening. If this post-deployed lengthening of the flex connectors is not large enough (based for the most part upon balloon lengthening with increasing pressure), the flex connector expansion will not compensate for the initial foreshortening. Accordingly, in order to minimize foreshortening, a design that minimizes the axial compressibility of the flex connector, while minimizing the flex connector ultimate compressibility is desired.

Figure 6A:
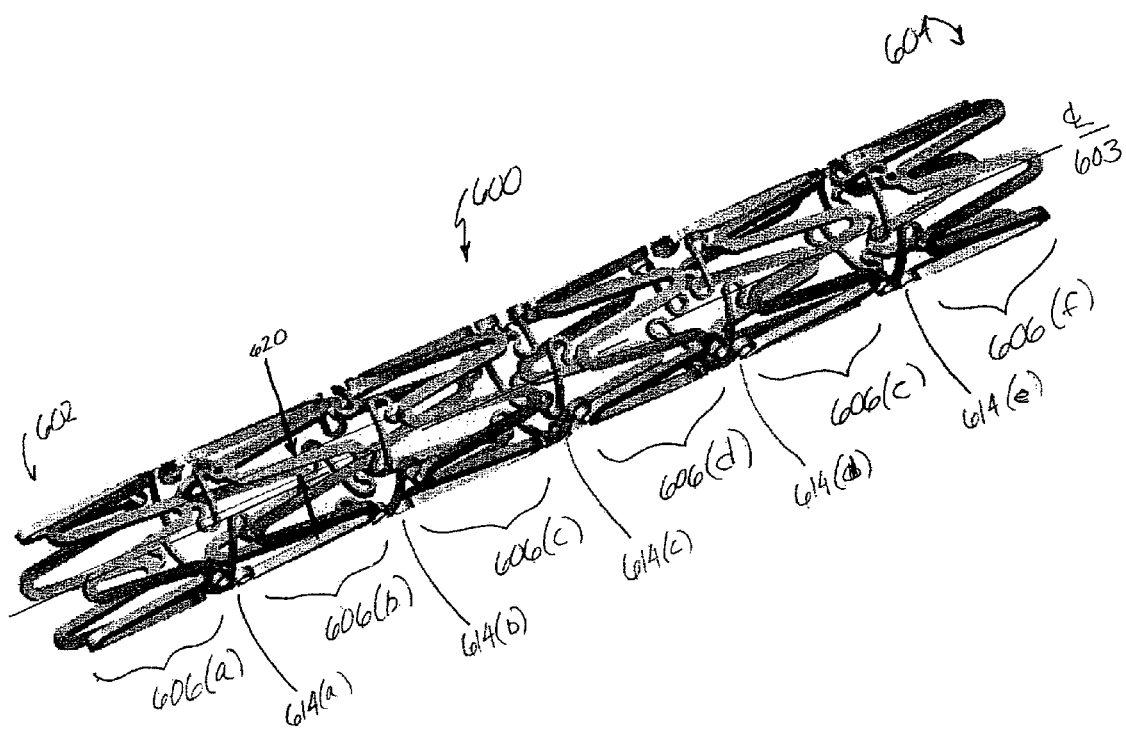
FIG. 6A is a perspective view of a stent according to one embodiment of the present invention.

One embodiment of the present invention that minimizes the axial compressibility of the flex links during stent deployment is illustrated in FIGS. 6A through 6G. FIG. 6A is a perspective view of a stent 600 according to one embodiment of the present invention. The stent 600 comprises a tubular configuration of structural elements having proximal and distal open ends 602, 604 respectively, and defining a longitudinal axis 603 extending there between. As described earlier, the stent 600 has a first diameter D1 for insertion into a patient and navigation through a vessel, and a second diameter D2 for deployment into the target area of a vessel. The second diameter D2 is thus greater than the first diameter D1.

The stent 600 structure is comprised of six (6) hoop sections 606(a) through 606(f) connected by five (5) flex links 614 sections or "sets" (i.e. 624(a) through 624(e)) extending between the proximal end 602 and the distal end 604. The flex links 614 connect adjacent hoops 606 together at flex link to loop connection regions 655, identified on FIG. 6C. The number of flex link sets 624 is typically one less than the number of hoop sections 606. Although six (6) hoop sections 606 and five (5) flex link sections 624 are shown for the purpose of example, one of skill in the art would understand that these numbers may be greater or smaller, to allow for longer or shorter stents 600 as would typically be required by the situation presented i.e., the type and size of the vessel, or location to be supported.

Figure 6B:
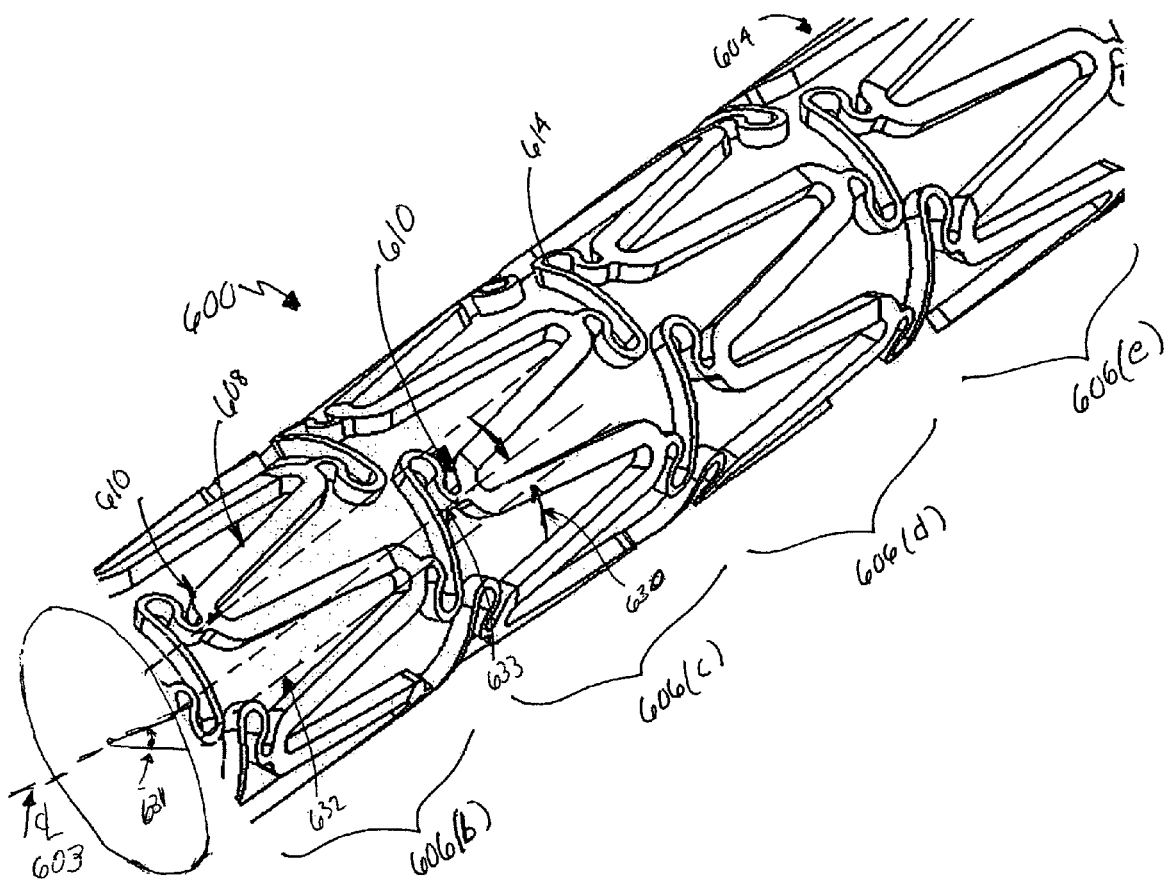
FIG. 6B is a magnified perspective views illustrating the structural elements comprising a stent according to one embodiment of the present invention.

FIGS. 6B and 6C are magnified perspective views illustrating the structural element comprising stent 600 according to one embodiment of the present invention. Each hoop section 606(a) through 606(f) includes a plurality of longitudinally arranged strut members 608 and a plurality of loop members 610 connecting adjacent struts 608. Adjacent struts 608 are connected at opposite ends in a substantially S or Z shaped pattern so as to form a plurality of cells. However, one of skill in the art would recognized that the pattern shaped by the struts is not necessarily a limiting factor in this invention, and other shaped patterns may be used. The plurality of loops 610 have a substantially semi-circular configuration and are substantially symmetric about their centers.

Each flex link 614 comprises two generally longitudinally extending "S" shaped double curved segments 621, one on each end, connected by one generally circumferentially extending strut segment 619. In one embodiment of the invention, the double curved S segment 621 comprises a first curve 622 and an opposingly oriented second curve section 623, wherein the first curve 622 is of a smaller radius than the second curve section 623. Each curved segment 621 of each flex link 614 is attached at one end to curved loop members 610 on adjacent hoop sections 606 at attachment points 655 as shown. The strut segments 619 are all oriented in the same direction. That is to say, all strut segments 619 are substantially parallel to one another regardless of their relative position. This configuration is apparent when viewing the stent 600 in a 2-dimensional configuration.

FIG. 6D illustrates the stent 600 according to one embodiment of the present invention, as it would appear if it were cut longitudinally and then laid out flat in a 2-dimensional configuration. It should be clearly understood that the stent 600 depicted in FIG. 6D is in fact cylindrical in shape, as depicted in FIG. 6A, and is only shown in the flat configuration for the purpose of illustration. This cylindrical shape would be obtained by rolling the flat configuration of FIG. 6D into a cylinder with the top points "C" jointed to the bottom points "D".

Stent 600 depicted in FIG. 6D illustrates the relationship between hoop sections 606(a) though 606(f) and flex link sets 624. That is, the fully connected configuration of stent 600 comprises multiple longitudinally spaced sets of hoop sections 606 interconnected by sets of flex links 624. Each set of flex links 624 comprises multiple circumferentially spaced flex links 614, with each flex link 614 in the set of flex links 624 connected to two curved loop members 610 of adjacent hoop sections 606. The number of flex links 614 in the set of flex links 624 is no more than one-half of the total number of curved loop members 610 in the loop sections 606.

Except at the extreme ends of the stent 600, every curved loop member 610 in adjacent hoops 606 is attached to a flex link 614. As earlier described, a stent 600 that is fully connected is called a closed cell stent. However, one of skill in the art would understand that other open and closed cell designs are also contemplated by the present invention, such that every curved loop member 610 may not be attached to a flex link 614. For example, the connections between the hoop structures 606 and the adjacent flex link 614 may be made at every other loop member 610; or alternatively, at a subset of the loop members 610 around the circumference of the hoop 606 in some defined pattern.

To reduce the axial compressibility of the flex links 614, each hoop section 606 is circumferentially phased or offset relative to the adjacent hoop section 606. For example, hoop section 606(a) is circumferentially phased relative to hoop section 606(b), and so on. This configuration causes the flex link to loop connection regions 655 on adjacent hoop sections to be out of axial alignment, which minimizes axial compressibility.

For the purpose of this invention, circumferentially phased hoop sections means that adjacent hoop sections are rotated or offset relative to one another about a longitudinal centerline 603 in stent 600. FIG. 6B is a close-up perspective view of the stent 600 illustrating the relative phase angle 631 between hoop sections 606(b) and 606(c). Reference line 632 is a longitudinal line, parallel to the stent 600 longitudinal axis 603, drawn through the apex of one particular loop member 610 on hoop 606(b). Similarly, reference line 633 is a longitudinal line, parallel to the stent 600 longitudinal axis 603, drawn through the apex of the corresponding adjacent loop member 610 on hoop 606(c). The distance 630 is the circumferential offset or arc between hoop section 606(b) and 606(c). The circumferential offset corresponds to a phase angle 631 illustrated in FIG. 6B.

As previously disclosed, the phased hoop sections 606 result in adjacent flex link to loop connection regions 655 being out of axial alignment. As a result, each loop 621 of the flex link 614 can interlock with the loop 621 of the circumferentially adjacent flex link 614 when the stent 600 is nested or crimped. In addition, the interlock between loop members 621 causes direct contact between the strut members 619 from circumferentially adjacent flex links 614. This direct contact provides compressive resistance between adjacent flex links 614 in a given flex link set 624, and decreases the lateral distance each flex link 614 may compress during stent deployment. The end effect of this compressive resistance is a stent with a lower foreshortening during deployment. In one embodiment of the invention, foreshortening was reduced by approximately 3 percent over a similar stent without phased hoop structures.

To accommodate for the circumferential phase between adjacent hoop sections 606, the flex connectors 614 are necessarily longer. In particular, each flex connector 614 in the illustrated embodiment has a longer circumferential strut member 619. There are several benefits of this configuration. For example, the longer circumferential strut member 619 provides a larger contact area between circumferentially adjacent flex connectors 614 when the stent 600 is in the crimped configuration. The larger contact area causes greater compressive resistance against foreshortening, providing a stent 600 having greater axial stiffness. In addition, the longer circumferential strut 619 will have a greater tendency to bend in a direction perpendicular to the stent 600 longitudinal axis, which improves the flex connector 614 flexibility, which is particularly useful when the stent is being navigated through tortuous vessel anatomies.

FIGS. 6E through 6G are partial close-up views of circumferentially adjacent flex link 614 according to one embodiment of the present invention. FIG. 6E illustrates the relationship between circumferentially adjacent flex links 614 when the stent 600 is in the cut, fully expanded configuration. The loop members 610 of adjacent hoop sections 606 are circumferentially phased; resulting in circumferential offset distance 630. As can be seen, even with the offset 630, there is no interlock region when the stent 600 is fully expanded.

FIG. 6F illustrates the stent 600 in a partially crimped configuration. As shown, the interlock region 640 between adjacent circumferential struts 619 begins to form, due in pertinent part, to the circumferential offset between the adjacent hoop sections 606. By comparing FIGS. 6E and 6F, it is apparent that the interlock region 640 is closely related to the circumferential offset 630 between the hoop sections. Accordingly, the greater the offset, the greater the strut 619 length, which will allow for a greater circumferential offset 640. This interlock region 640 illustrated will allow for significant foreshortening resistance even when the stent 600 is partially crimped.

FIG. 6G illustrates the stent 600 in the fully nested position, crimped down and restrained onto the delivery member. In this configuration the S sections 621 of the flex links 614 fully nest in one another, providing a large interlock region 640 between adjacent circumferential struts 619. This large interlock region 640 provides a large area of physical contact between adjacent flex links 614, decreasing the lateral distance the flex link 614 may compress during stent deployment.

While a number of variations of the invention have been shown and described in detail, other modifications and methods of use contemplated within the scope of this invention will be readily apparent to those of skill in the art based upon this disclosure. It is contemplated that various combinations or sub combinations of the specific embodiments may be made and still fall within the scope of the invention.

The following claims are provided to illustrate examples of some beneficial aspects of the subject matter disclosed herein which are within the scope of the present invention.

What is claimed is:

1. An intraluminal prosthetic device comprising:
   a first hoop section having a first circumferential phase orientation along a longitudinal axis;
   a second hoop section having a second circumferential phase orientation along the longitudinal axis, wherein the first circumferential phase orientation is different than the second circumferential phase orientation; and
   a plurality of flex members being arranged in a spaced apart relationship about the circumference of the first and the second hoop sections, each flex member having a first and a second end, wherein the first end of each flex member is attached to the first hoop section at a first connection region, and the second end of each flex member is attached to the second hoop section at a second connection region, the first connection region and the second connection region associated with each flex member being circumferentially offset from axial alignment, each flex member further comprising two generally longitudinally extending curved segments, one on each extreme end of said flex member, connected by one generally circumferentially extending linear strut segment, wherein:
   (i) each longitudinally extending curved segment includes a first curved section having a first constant radius of curvature directly attached to an opposingly oriented second curved section having a second constant radius of curvature,
   (ii) the first curved section is directly attached to the first or the second hoop section and the second curved section is directly attached to the linear strut segment, and
   (iii) the linear strut segments on circumferentially adjacent flex members are configured to be in direct contact when the prosthetic device is in a crimped state.

2. The prosthetic device of claim 1 wherein the first and the second hoop sections include a plurality longitudinally arranged strut members and a plurality of loop members connecting adjacent struts.

3. The prosthetic device of claim 2 wherein each loop member has a substantially semi-circular configuration.

4. The prosthetic device of claim 3 wherein each loop member is substantially symmetric about its radial center point.

5. The prosthetic device of claim 2 wherein the connections between the hoop structure and the adjacent flex member is made at every loop member.

6. The prosthetic device of claim 2 wherein the connections between the hoop structure and the adjacent flex member is made at every other loop member along the circumference of the hoop structure.

7. The prosthetic device of claim 2 wherein the connections between the hoop structure and the adjacent flex member is made at a subset of the loop members around the circumference of the hoop structure in some defined pattern.

8. The prosthetic device of claim 1 wherein the first curve section has a smaller radius of curvature than the second curve section.

9. The prosthetic device of claim 1 wherein each linear strut segment is substantially parallel to the adjacent linear strut segment.

10. An intraluminal prosthetic device comprising:
    a first hoop section comprising a plurality of longitudinally arranged first strut members and a plurality of semicircular first loop members connecting circumferentially adjacent first strut members to form a closed endless ring;
    a second hoop section comprising a plurality of longitudinally arranged second strut members and a plurality semicircular second loop members connecting circumferentially adjacent second strut members to form a closed endless ring, wherein the first loop members are not axially aligned with the second loop members; and
    at least one flex member, each flex member having a first and a second end, wherein the first end of each flex member is attached to the first loop and the second end of each flex member is attached to the second loop, each flex member further comprising two generally longitudinally extending curved segments, one on each end of the flex member, connected by one generally circumferentially extending linear strut segment, wherein each longitudinally extending curved segment includes a first curved section directly attached to an opposingly oriented second curved section such that each first curved section is directly attached to the loops and each second curved section is directly attached to the linear strut segment.

11. An intraluminal prosthetic device comprising:

a first endless hoop section having a first circumferential phase orientation along a longitudinal axis;

a second endless hoop section having a second circumferential phase orientation along the longitudinal axis, wherein the first circumferential phase orientation is different than the second circumferential phase orientation; and a plurality of flex members being arranged in a spaced apart relationship about the circumference of the first and the second hoop sections, each flex member having a first and a second end, wherein the first end of each flex member is attached to the first hoop section at a first connection region, and the second end of each flex member is attached to the second hoop section at a second connection region, the first connection region and the second connection region associated with each flex member being circumferentially offset from axial alignment, each flex member further comprising two generally longitudinally extending curved segments, one on each extreme end of said flex member, connected by one generally circumferentially extending straight linear strut segment, wherein each longitudinally extending curved segment includes a first curved section directly attached to an opposingly oriented second curved section, and wherein the linear strut segments on circumferentially adjacent flex members are configured to be in direct contact when the prosthetic device is in a crimped state.

\* \* \* \* \*